United States Patent [19]
Watanabe et al.

[11] Patent Number: 5,571,937
[45] Date of Patent: Nov. 5, 1996

[54] COMPLEMENTARY DNA AND TOXINS

[75] Inventors: Kyoichi A. Watanabe, Port Chester; Wu-Yun Ren, New Rochelle, both of N.Y.; Roger Weil, Geneva, Switzerland

[73] Assignees: Sloan-Kettering Institute for Cancer Research, New York, N.Y.; ZW Biomedical Research AG, Bern, Switzerland

[21] Appl. No.: 242,664

[22] Filed: May 13, 1994

[51] Int. Cl.⁶ ................... C07F 9/22; C07F 9/28; C07C 321/00; C07C 323/00
[52] U.S. Cl. ................ 560/147; 562/9; 562/10; 562/11
[58] Field of Search .............. 560/147; 562/9, 562/10, 11

[56] References Cited

U.S. PATENT DOCUMENTS

| | | | |
|---|---|---|---|
| 3,970,586 | 7/1976 | Schliebs et al. | 562/4 |
| 4,456,464 | 6/1984 | Lee et al. | 562/11 |
| 5,273,969 | 12/1993 | Biller et al. | 558/155 |
| 5,300,679 | 3/1994 | Baylis et al. | 558/155 |

OTHER PUBLICATIONS

Hall, R. H., et al., Nucleotides. Part XLI. Mixed Anhydrides as Intermediates in the Synthesis of Dinucleoside Phosphates. Journal of the Chemical Society (1957) 644: 3291–3296;.

Letsinger, R. L. and Schott, M. E., Selectivity in Binding a Phenanthridinium–Dinucleotide Derivative to Homopolynucleotides. J. Am. Chem. Society (1981) 103(24): 7394–7396;.

Letsinger, R. L. and Lunsford, W. B., Synthesis of Thymidine Oligonucleotides by Phosphite Triester Intermediates. J. Am. Chem. Soc. (1976) 98(12): 3655–3661;.

Toulme, J. J. and Helene, C., Antimessenger Oligodeoxyribonucleotides: An Alternative to Antisense RNA for Artificial Regulation of Gene Expression–A Review. Gene (1988) 72: 51–58;.

Uhlmann, E. and Engels, J., Chemical 5'-Phosphorylation of Oligonucleotides Valuable in Automated DNA Synthesis. Tetrahedron Letters (1986) 27(9): 1023–1026;.

Primary Examiner—Nathan M. Nutter
Attorney, Agent, or Firm—John P. White

[57] ABSTRACT

This invention relates to new derivatized solid supports and compounds having the formula:

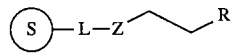

wherein S may be a solid support; L may be a chemical bond or a suitable inorganic or organic linker; Z may be $-SO_2-$ or $-S-S-$; R may be $-OH$, an H-phosphonate, an alkanephosphonate, a phosphotriester, a phosphite triester, a phosphite diester, a phosphorothioate, a phosphorodithioate, a phosphoroamidate, a phosphoroamidite, $-OR^1$ $-SR^1$, a nucleotide, N, which may be substituted or modified in its sugar, phosphate or base or an oligonucleotide of the formula $-(N)_g$, $-R^2$, wherein N is as defined above which may be the same or different; g is an integer from one to two hundred; $R^1$ is a suitable protecting group; and $R^2$ may be an H-phosphonate, an alkane-phosphonate, a phosphotriester, a phosphite triester, a phosphite diester, a phosphorothioate, a phosphorodithioate, a phosphoroamidate, a phosphoroamidite, $-OH$, $-OR^1$, $-SR^1$, or $-O-P(OCH_2CH_2CN)-O-CH_2CH_2ZCH_2CH_2OR^1$. Furthermore, this invention provides methods for preparing 3'-phosphate oligonucleotides, 5'-phosphate oligonucleotides, (3',5')-diphosphate oligonucleotides, 3'-phosphate oligonucleotide conjugates, 5'-phosphate oligonucleotide conjugates, and (3',5')-diphosphate oligonucleotide conjugates.

3 Claims, 6 Drawing Sheets

Pyr:Pur:Pyr

Pyr:pur:pur

COMPLEMENTARY DNA AND TOXINS

The invention described herein was made in part with government funds under Grant Nos. CA18601 and CA33907 from the National Cancer Institute, National Institutes of Health, U.S. Department of Health and Human Services. Therefore, the U.S. Government has certain rights in this application.

Throughout this application various references are cited by author and publication year. The full citations are listed alphabetically and may be found immediately preceding the claims. These publications are hereby incorporated by reference into the present application.

BACKGROUND OF THE INVENTION

The proposition that an oligonucleotide could be used as a therapeutic agent was described in 1978 by Zamecnik and Stephenson in a study on the growth inhibition of Rous sarcoma virus [Zamecnik, Stephenson; 1978]. Since that time, there has been a great interest in unmodified and modified oligonucleotides. As a result, new synthetic methods to selectively design oligonucleotides are important. Therapeutic oligonucleotides which interact specifically with a target mRNA by Watson-Crick base pairing are known as antisense oligonucleotides. Therapeutic oligonucleotides which interact with genomic DNA by means of Hoogsteen base pairing in the major groove, forming a triple helix, are known as triplex oligonucleotides.

In order for an oligonucleotide to be an effective therapeutic agent, the following issues must be considered: (1) cellular uptake; (2) degradation (by intracellular exo-and endonucleases); (3) triplex stability; and (4) triplex specificity [Gelsow, 1991; Henene, 1991; Stein, 1993]. Most of these issues are addressed by modifying the various components of an oligonucleotide [Uhlmann, 1990]. For example, one important modification is the phosphorylation of the 3' and 5' end of an oligonucleotide to produce a 3',5'-diphosphate oligonucleotide. A 3',5'-diphosphate oligonucleotide not only provides protection against intracellular degradation, it also allows for the easy attachment of useful functional groups. These attached functional groups may be used to increase the effectiveness in therapy.

Currently, there are methods to produce oligonucleotides phosphorylated at the C-3' terminal [Gough, 1983; Volkov, 1988; Felder, 1984]—and methods to produce oligonucleotides phosphorylated at the C-5' terminal [Uhlmann, 1986] —however, there are no simple methods available for the preparation of an oligonucleotide phosphorylated on both ends of the chain. In addition, most of the phosphorylation methods are incompatible with phosphoroamidite chemistry, and hence incompatible with most automatic DNA synthesizers. For example, one successful phosphorylation method is achieved by enzymatic means with polynucleotide kinase and ATP [Maniatis, 1982]. Thus, improved phosphorylation methods are needed—especially those that can work on an automatic DNA synthesizer.

This invention demonstrates a simple method for the preparation of oligonucleotides phosphorylated on both ends of the chain (i.e.: 3',5'-diphosphate oligonucleotides) In addition, this method is well suited for use in an automatic DNA synthesizer.

SUMMARY OF THE INVENTION

This invention relates to derivatized solid supports having the formula:

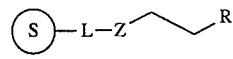

wherein S may be a solid support;

L may be a chemical bond or a suitable inorganic or organic linker;

Z may be —$SO_2$— or —S—S—; R may be —OH, an H-phosphonate, an alkane-phosphonate, a phosphotriester, a phosphite triester, a phosphite diester, a phosphorothioate, a phosphorodithioate, a phosphoroamidate, a phosphoroamidite, —$OR^1$, —$SR^1$, a nucleotide, N, which may be substituted or modified in its sugar, phosphate or base, or an oligonucleotide of the formula —$(N)g$—$R^2$, wherein N is as defined above which may be the same or different;

g is an integer from one to two hundred;

$R^1$ is a suitable protecting group; and $R^2$ may be an H-phosphonate, an alkane-phosphonate, a phosphotriester, a phosphite triester, a phosphite diester, a phosphorothioate, a phosphorodithioate, a phosphoroamidate, a phosphoroamidite, —OH, —$OR^1$, —$SR^1$, or —O—$P(OCH_2CH_2CN)$—O—$CH_2CH_2ZCH_2$ $CH_2OR^1$. Furthermore, this invention provides methods for preparing 3'-phosphate oligonucleotides, 5'-phosphate oligonucleotides, (3',5')-diphosphate oligonucleotides, 3'-phosphate oligonucleotide conjugates, 5'-phosphate oligonucleotide conjugates, and (3', 5')-diphosphate oligonucleotide conjugates.

DETAILED DESCRIPTION OF THE INVENTION

Figure 1A:
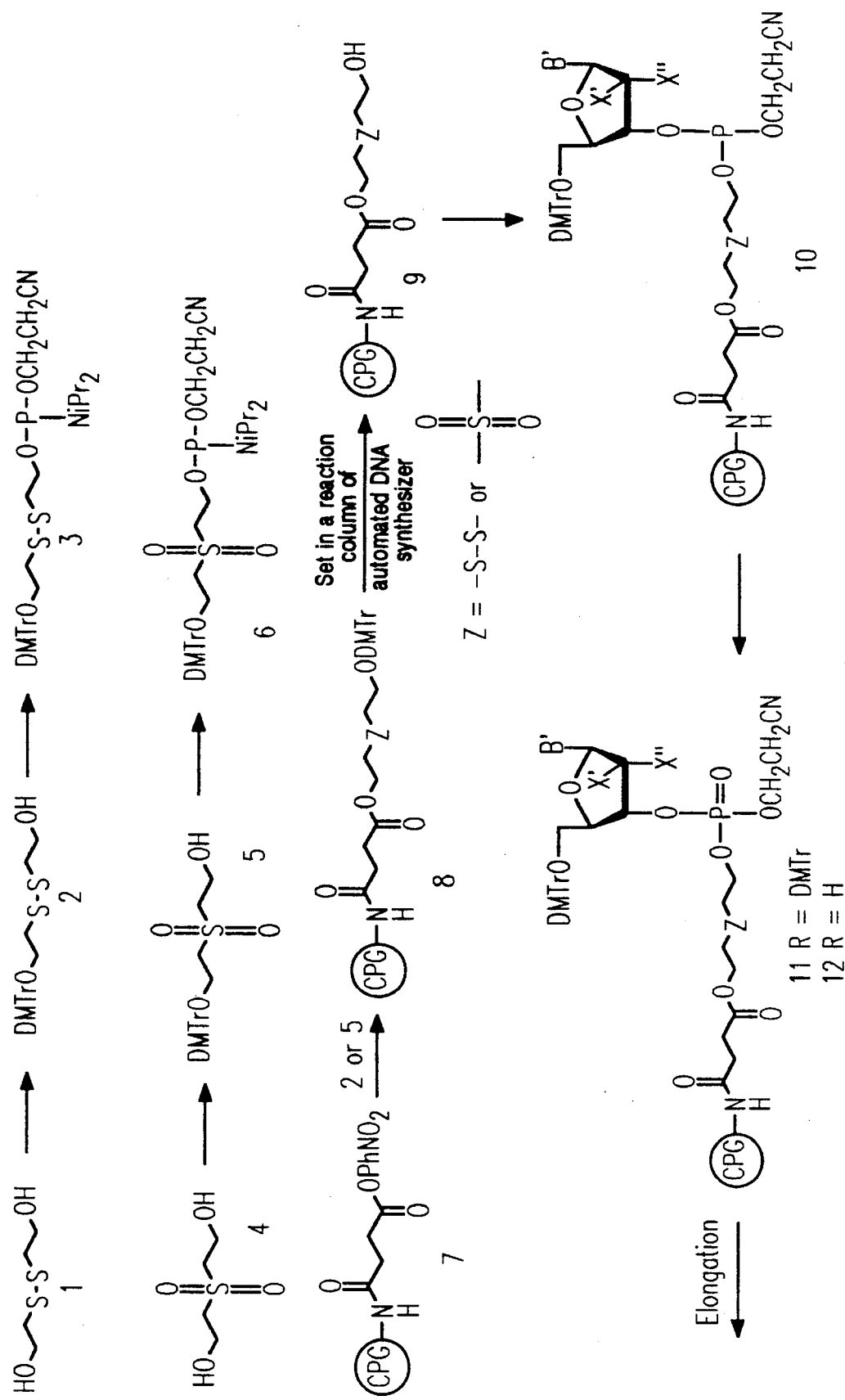
FIGS. 1A and 1B: A synthetic scheme for the synthesis of an oligonucleotide phosphorylated on both the C-3' and C-5' ends.

This invention relates to derivatized solid supports having the formula:

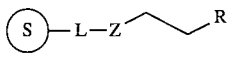

wherein S may be a solid support;

L may be a chemical bond or a suitable inorganic or organic linker;

Z may be —$SO_2$— or —S—S—;

R may be —OH, an H-phosphonate, an alkane-phosphonate, a phosphotriester, a phosphite triester, a phosphite diester, a phosphorothioate, a phosphorodithioate, a phosphoroamidate, a phosphoroamidite, —$OR^1$, —$SR^1$ a nucleotide, N, which may be substituted or modified in its sugar, phosphate or base, or an oligonucleotide of the formula —$(N)_g$—$R^2$, wherein N is as defined above which may be the same or different; g is an integer from one to two hundred; $R^1$ is a suitable protecting group; and $R^2$ may be an H-phosphonate, an alkane-phosphonate, a phosphotriester, a phosphite triester, a phosphite diester, a phosphorothioate, a phosphorodithioate, a phosphoroamidate, a phosphoroamidite, —OH, —$OR^1$, —$SR^1$, or —O—P($OCH_2CH_2CN$)—O—$CH_2CH_2ZCH_2CH_2OR^1$.

Further, this invention relates to a compound having the formula:

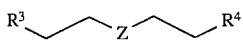

wherein $R^3$ is a suitable protecting group; Z is —$SO_2$— or —S—S—; and $R^4$ is —OH, a H-phosphonate, an alkane-phosphonate, a phosphite diester, a phosphite triester, a phosphotriester, a phosphorothioate, a phosphorodithioate, a phosphoroamidate, or a phosphoroamidite.

Further, this invention relates to a compound having the formula:

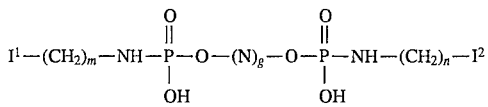

wherein $I^1$ and $I^2$ may each independently be a compound having the formula:

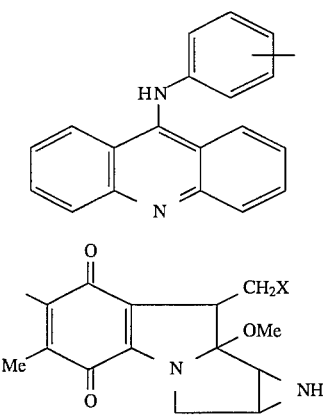

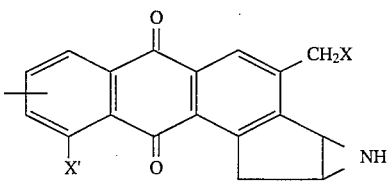

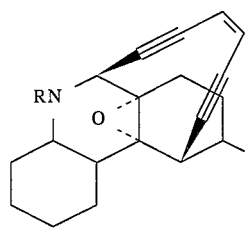

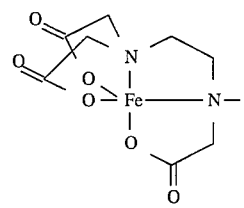

wherein X is —O—CO—NH—Y, wherein Y is —H, $C_1$–$C_{10}$ alkyl which may independently be straight chain or branched, substituted or unsubstituted, a benzyl which may be substituted or unsubstituted, X' is —H, —OH, —$OCH_3$; R is —H, $C_1$–$C_{10}$ alkyl which may independently be straight chain or branched, substituted or unsubstituted; g is an integer from one to two hundred; N is a nucleotide which may be the same or different and substituted or modified in its sugar, phosphate or base; —$(N)_g$— is an oligonucleotide which may be TTCCTCCTGCGG (SEQ ID NO: 3), CCCG-GCCTGCGA (SEQ ID NO: 4), AATGGTAAAATGG (SEQ ID NO: 5), TTCCTCCTGCGG (SEQ ID NO: 6), CCCG-GCCTGCGA (SEQ ID NO: 7), CGGTGGCGCTGCG-CAAGGTAAAACGC (SEQ ID NO: 8), ACACGAATTT-TATTTAATAC (SEQ ID NO: 9), ATGACTGAATA (SEQ ID NO: 10), CTTAGGAC, and GGCGCTGCGCAAGG-TAAAA (SEQ ID NO: 11), or an oligonucleotide targeted to target sequences of the HIV-1 proviral genome (EMBL Gene Bank NREHTLV3, accession number X01762) which may be $_{2698}$AGAAATGGAAAAGGAAGGGAAAA$_{2720}$ (SEQ ID NO: 1), $_{7051}$AGAAGAAGAGGTAGTAA$_{7067}$ (SEQ ID NO: 2), AGGAGAAAGAGA (SEQ ID NO: 12), AGAA-GAAGAAGG (SEQ ID NO: 13), AAAAAAGAAAAAA (SEQ ID NO: 14), AAAAAAGGAAAAGG (SEQ ID NO: 15), GGAGGAAAAAGAGA (SEQ ID NO: 16), GGAGAAAGGAGAGA (SEQ ID NO: 17), AGAGAGAAAAAAGAG (SEQ ID NO: 18), AAGAG-GAGGAGGAGG (SEQ ID NO: 19), AGGGGGAAA-GAAAAAA (SEQ ID NO: 20), $_{4817}$AAAA-GAAAGGGGGA$_{4832}$ (SEQ ID NO: 21), $_{9098}$AAAAGAAAAGGGGGA$_{9113}$ (SEQ ID NO: 22), GGAAAAGGAAGGGAAAA (SEQ ID NO: 23), GGCA-GAAGAAGAGG (SEQ ID NO: 24), AAGAAAAGAAT-GAA (SEQ ID NO: 25), AAGATAGAGGAAGAG (SEQ ID NO: 26), AGAGGAAGAGCAAAA (SEQ ID NO: 27), AGGAAGAAGCGGAGA (SEQ ID NO: 28), GAAAGC-GAAAGGGAAA (SEQ ID NO: 29), AAAAGTAA-GAAAAAAG (SEQ ID NO: 30), GAGAGTGAAG-GAGAAA (SEQ ID NO: 31), AGAAGGAGAGAGATGGG (SEQ ID NO: 32), AATAAAAAAGGAAAGG (SEQ ID NO: 33), AAGAAGAAAAGCAAAGA (SEQ ID NO: 34), GCAGAGAGAAAAAAGAG (SEQ ID NO: 35), GAAGGAATAGAAGAAGAAGG (SEQ ID NO: 36), AAGAGGAGGAGGAGGTGGG (SEQ ID NO: 37), GGAGAAAGGAGAGATAAAAAA (SEQ ID NO: 38), AGAAGAAGAAGGTGGAGAGAGAGA (SEQ ID NO: 39), AAGAAAAGAATGAACAAGAA (SEQ ID NO: 40), GAAGGAATAGAAGAAGAAGGTGGAGAGAGAGA (SEQ ID NO: 41); and m and n may each independently be an integer from one to five.

In addition, this invention provides a method of preparing a 5'-phosphate oligonucleotide which comprises: (a) contacting a suitably protected oligonucleotide with a compound having the formula:

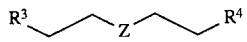

wherein $R^3$ is a suitable protecting group, Z is —$SO_2$— or —S—S—, $R^4$ is a phosphoroamidite, in an appropriate solvent so as to form a 5'-phosphate oligonucleotide precursor; and (b) treating the 5'-phosphate oligonucleotide precursor with an appropriate reagent so as to produce the 5'-phosphate oligonucleotide.

This invention further provides a method of preparing a solid support useful for preparation of a 3'-phosphate oligonucleotide which comprises: contacting a suitably functionalized solid support with a compound having the formula:

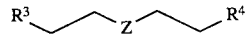

wherein $R^3$ is a protecting group, Z is —$SO_2$— or —S—S—, $R^4$ is —OH, in an appropriate solvent so as to form the solid support useful for the preparation of the 3'-phosphate oligonucleotide.

This invention further provides a method of preparing a 3'-phosphate oligonucleotide which comprises: (a) contacting a suitably protected nucleotide monomer with a derivatized solid support having the formula:

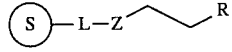

wherein S is a solid support, L is a chemical bond or an inorganic or organic linker, Z is —$SO_2$— or —S—S—, and R is OH, in an appropriate solvent so as to form a 3'-phosphate nucleotide precursor; (b) treating the 3'-phosphate nucleotide precursor with a second nucleotide monomer so as to produce an elongated 3'-phosphate nucleotide precursor; (c) repeating step (b) so as to produce a desired 3'-phosphate oligonucleotide precursor; and (d) working up the desired 3'-phosphate oligonucleotide precursor with an appropriate reagent so as to produce the 3'-phosphate oligonucleotide.

This invention further provides a method of preparing a 3',5'-diphosphate oligonucleotide which comprises: (a) contacting a suitably protected nucleotide monomer with a derivatized solid support having the formula:

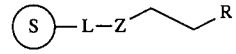

wherein S is a solid support, L is a chemical bond or an inorganic or organic linker, Z is —S—S— or —$SO_2$—, and R is OH, in an appropriate solvent so as to form a 3'-phosphate nucleotide precursor; (b) treating the 3'-phosphate nucleotide precursor with a second nucleotide monomer so as to produce an elongated 3'-phosphate nucleotide precursor; (c) repeating step (b) so as to produce a desired 3'-phosphate oligonucleotide precursor; (d) reacting the desired 3'-phosphate oligonucleotide precursor with a compound having the formula:

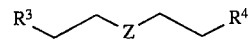

wherein $R^3$ is a suitable protecting group, Z is —$SO_2$— or —S—S—, and $R^4$ is a phosphoroamidite, in an appropriate solvent so as to form a 3',5'-diphosphate oligonucleotide precursor; and (e) working up the 3',5'-diphosphate oligonucleotide precursor with an appropriate reagent so as to produce the 3',5'-diphosphate oligonucleotide.

In the compounds and methods above, the solid support may be controlled pore glass (CPG), polystyrene resin, polyamide resin, silica gel, polydimethylacrylamide resin and the like. The solid supports may be of a variety of forms such as small beads, pellets, disks or other convenient forms.

In the compounds and methods above, the organic linker is —NH—CO—$CH_2CH_2$—CO—O—$CH_2CH_2$— and the like.

As used herein, chemical linkers serve to link a specific compound to a solid support. A chemical linker may be a component of a derivatized or functionalized solid support. The use of linkers are well known in the art, and may be varied depending upon the solid support, specific compound to be linked, and method employed to synthesize an oligonucleotide.

In one embodiment, the functionalized solid support is S—NH—CO—$CH_2CH_2$—CO—$OPhNO_2$ wherein Ph is Phenyl and S is controlled pore glass. In addition, many modifications can be made in the functionalized solid support and may include, but are not limited to, changing the length of the alkyl group such that the above linker is —NH—CO—$(CH_2)_n$—CO—$OPhNO_2$, other activated carboxylic acid such as pentafluorophenyl ester, and imidazoles.

The nucleotide may be a deoxyribonucleotide or a ribonucleotide, and the base may be adenine, guanine, cytosine, uracil, thymine or hypoxanthine. Other modifications made in the nucleotide or oligonucleotide may include, but are not limited to, adding substituents such as —F, —$NH_2$, —OH, —$OCH_3$, —SH, —$SCH_3$; derivatizing the phosphate group to a phosphorothioate, a phosphorodithioate, an alkylphosphonate, a phosphoroamidate, or a phosphoroamidite; and replacement of the phosphate group with siloxane, sulfonamide, thioformal, sulfide, hydroxylamine, amide, ethylene glycol, carbonate, carboxymethyl, acetamidate, carbamate, or thioether.

As used herein, a phosphoroamidite has the general formula, —P(N($R_b$)$_2$)(O$R_a$) where $R_a$ and $R_b$ may include, but are not limited to, alkyl and alkyl-CN.

Preferably, the phosphoroamidite is —O—P(O$CH_2CH_2$CN)—N($C_3H_7$)$_2$.

As used herein, a protecting group is a substituent that is specially chosen to not react during a particular chemical reaction. Protecting groups are routinely added and removed, and is well known in the art as protecting and deprotecting respectively. As an example, during the synthesis of an oligonucleotide, a 5' hydroxyl group of a 3'-phosphoroamidite nucleotide monomer is protected using 4,4'-dimethoxytrityl; the 5' protecting group is then deprotected to give back the 5' hydroxyl. Protecting groups are well known in the art and can vary depending upon the method used to synthesize an oligonucleotide. Standard protecting groups include, but are not limited to, Di-p-anisylphenylmethyl and 4,4'-dimethoxytrityl.

As used herein, oligonucleotides that are covalently linked to a intercalator or cross-linker are known as an oligonucleotide conjugate. The oligonucleotide conjugates may be further linked to lipophilic carriers, peptide conjugates, and terminal transferases.

In the above methods, an appropriate reagent may consist of oxidation by iodine/water followed by treatment with 40% aqueous ammonia.

In the above methods, step (c) may be performed on an automatic DNA synthesizer. DNA synthesizers are well known in the art, and the specific DNA synthesizer employed may be varied depending upon factors such as the chemical modifications made in the base, sugar, or phosphate of a nucleotide. The DNA synthesizer may use the well-established phosphoroamidite procedure.

In the above methods, a suitably protected oligonucleotide may have a free 5' hydroxyl group with protecting groups replacing all other free hydroxyl groups. In one embodiment, the suitably protected oligonucleotide is attached to a solid support.

In one embodiment, the suitably protected oligonucleotide is attached to a solid support; in another embodiment, the suitably protected nucleotide monomer is a suitably protected phosphoroamidite nucleotide monomer.

In the methods above, the 3',5'-diphosphate oligonucleotide precursor may be attached to a solid support.

In the above methods, a 3'-phosphate nucleotide precursor, an elongated 3'-phosphate nucleotide precursor, and a desired a 3'-phosphate oligonucleotide precursor may have a free 3' or 5' hydroxyl group or a protecting group at the 3' or 5' end. The free 3' or 5' hydroxyl group may have resulted from a standard deprotection step; and a protecting group at the 3' or 5' end may have resulted from a standard protection step. In addition, the free 3' or 5' hydroxyl group may be reacted with a phosphoroamidite.

In the above methods, a suitably protected nucleotide monomer or nucleotide monomer may be, but is not limited to, PheAc-DMT-deoxylnucleoside CED phosphoramidite, iBu-DMT-deoxylnucleoside CED phosphoramidite, Bz-DMT-deoxylnucleoside CED phosphoramidite, and DMT-deoxylnucleoside CED phosphoramidite (where DMT is 4,4'-dimethoxytrityl, CED is 2-cyanoethyl diisopropyl, Bz is benzoyl, and PheAc is Phenoxyacetyl).

In one embodiment, the 5'-phosphate oligonucleotide is further treated with a reactive conjugate in an appropriate solvent so as to form a 5'-phosphate oligonucleotide conjugate; in another embodiment, the 3'-phosphate oligonucleotide is further treated with a reactive conjugate in an appropriate solvent so as to form a 3'-phosphate oligonucleotide conjugate; and in a further embodiment, the 3',5'-diphosphate oligonucleotide is further treated with a reactive conjugate in an appropriate solvent so as to form a 3',5'-diphosphate oligonucleotide conjugate.

In one embodiment, the intercalator may be an acridine derivative. In another embodiment, the cross-linker may be a Mytomycin C derivative, an anthraquinone derivative, an enediyne derivative or a metal chelate.

In the above methods, an appropriate solvent or reagent may include, but is not limited to, 1H-tetrazole in acetonitrile, DMF, water, triphenylphosphine, 2,2'-dipyridyldisulfide and combinations thereof.

The oligonucleotide conjugates may be used as "smart biological bombs" (see below) which may be programmed to find and inactivate specific genes on the HIV DNA. The same "bombs" may be reprogrammed (see below) to recognize and interact with specific DNA sequences (viral genes) such as present in the human papillomavirus; chronic infection with this virus plays a causative role in the development of some human cancers [Marks, 1993]. The biological "bombs" can also be used to inactivate other viruses in man or animal which contain as genomes DNA or which reverse transcribe their RNA genome into DNA. Finally, the "bombs" may be reprogrammed to find and inactivate human or animal genes playing a causative role in certain pathological conditions.

The specificity of the "bombs" is expected to be very high; they should recognize and interact only with one out of 20,000–30,000 genes (i.e. the number of total genes in a human cell) and thus theoretically only inactivate the single target gene [Moser, 1987; Strobel, 1990; Beal, 1991; Geisow, 1991; Henene, 1991].

Two types of "bombs" have been developed: one carries a "warhead" (see below) which cleaves the target gene whereas the other type of "warhead" binds covalently and irreversibly to the target gene. In both instances the target genes are expected to become irreversibly inactivated. Obviously, two or more "bombs" can be used which will be targeted to different DNA sequences on the same or other genes of HIV. Specific HIV DNA sequences will be used to test the in vitro effects of the "bombs" and their capacity to prevent HIV production in HIV-infected human cells.

One of the main difficulties to be expected is related to the fact that the main reservoirs for chronic HIV production are broadly distributed cells such as macrophages (and others) which are present in different organs such as the liver, spleen etc.

The "bombs" may be packed into well-known delivery systems specific for certain cell types. For example, HIV-infected human macrophages kept in tissue cultures may be targeted using "bombs" that are packed into nanoparticles.

MOLECULAR AND CHEMICAL PROPERTIES OF THE "BIOLOGICAL BOMBS"

Figure 1B:
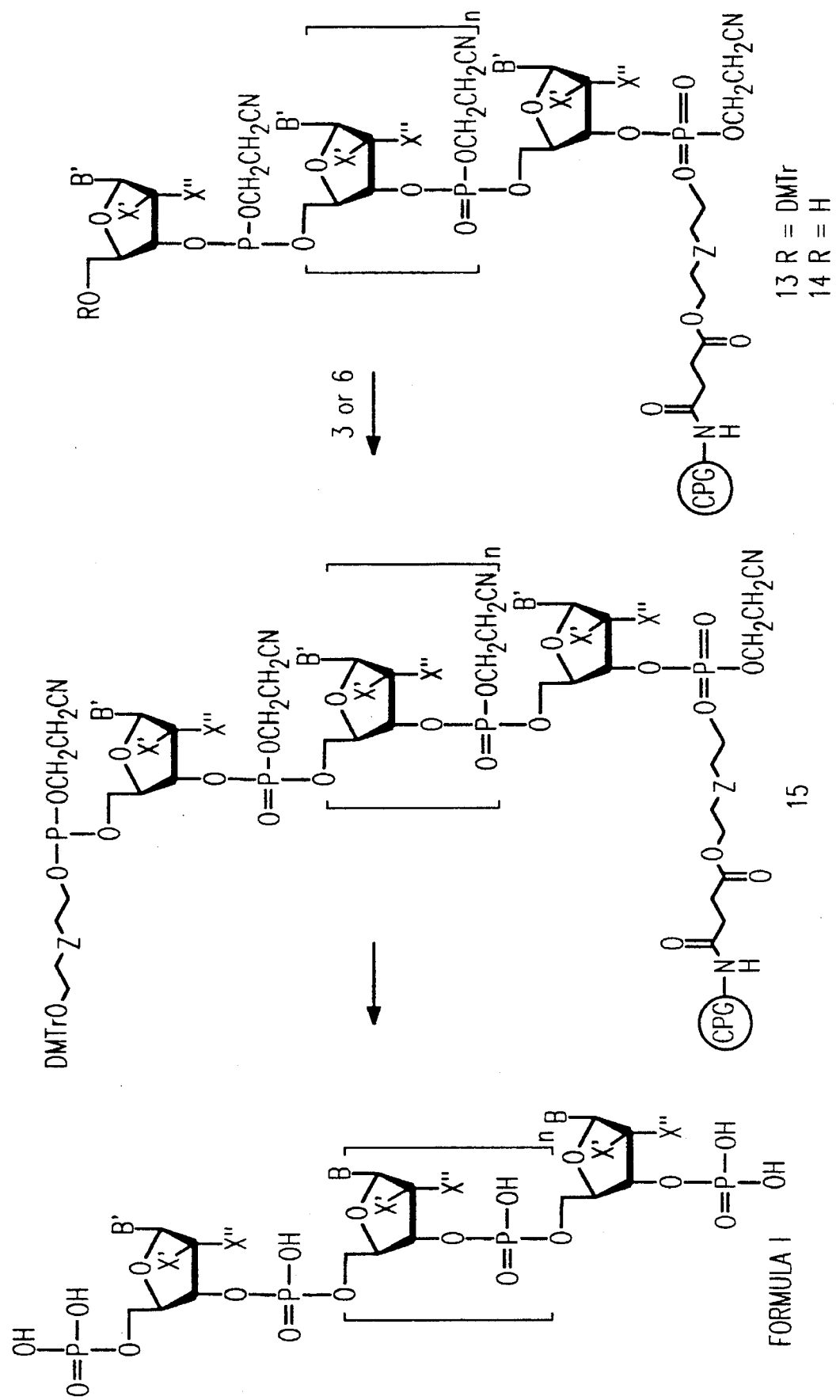
Figure 4:
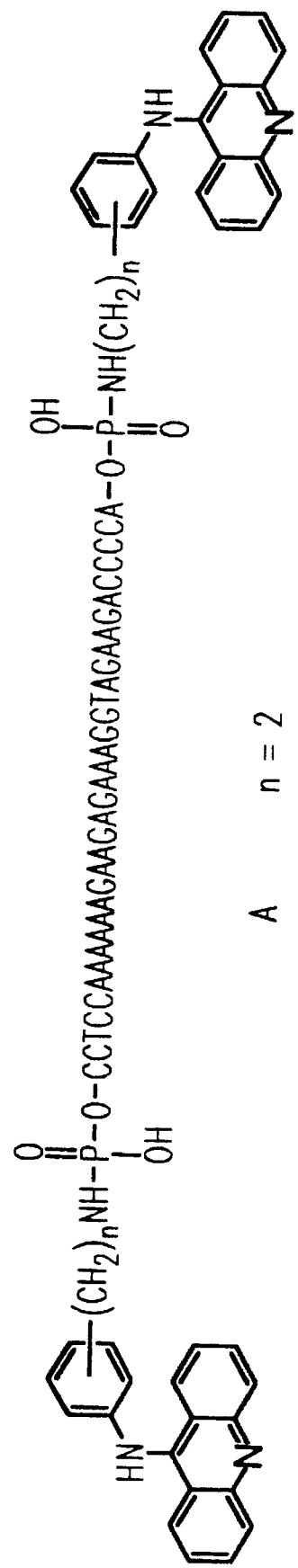
FIG. 4: An oligonucleotide (directed against the early gene of the SV40 tumor virus) to which an intercalating acridine derivative was fixed to both termini.
Figure 5A:
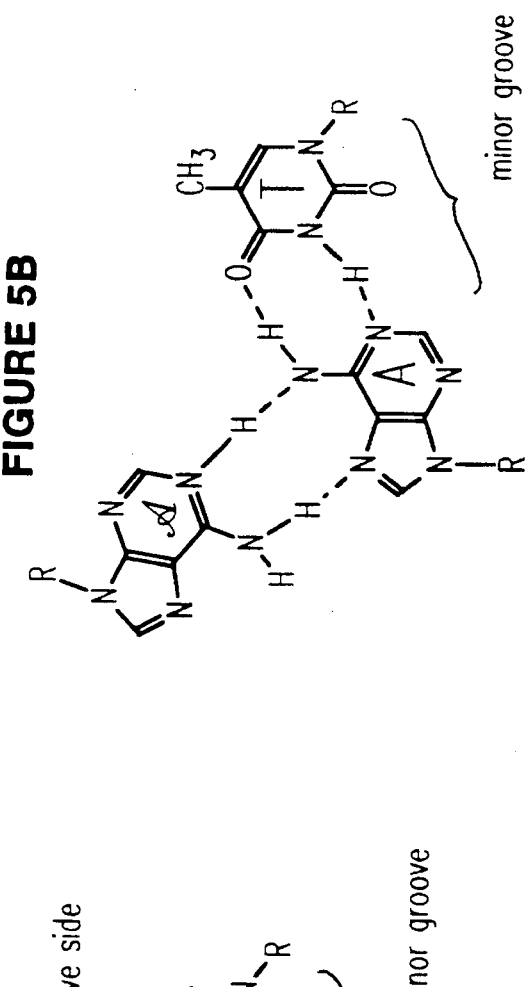
FIG. 5: Two distinct structural classes of triple helices for double helical DNA recognition.
Figure 5B:
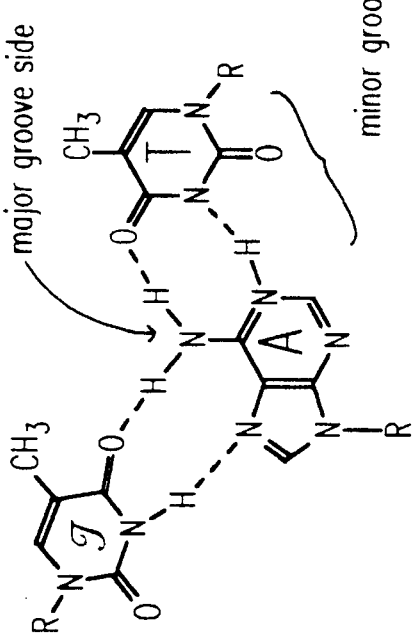
Figure 5C:
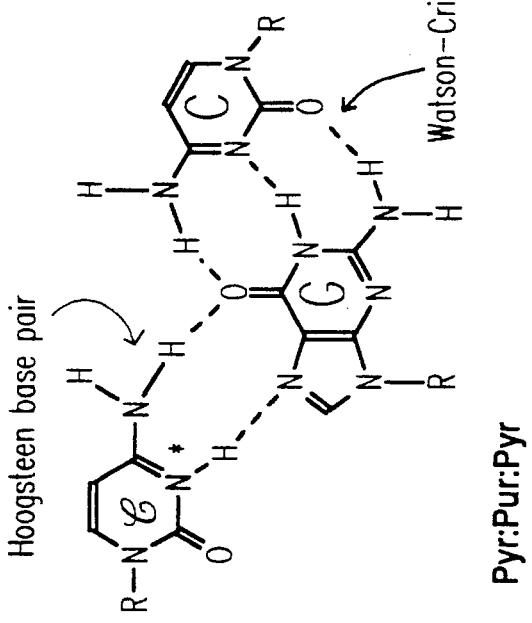
Figure 5D:
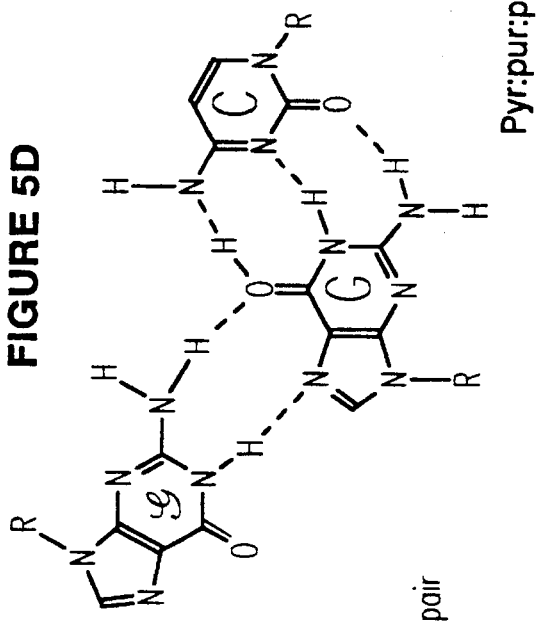

All "bombs" now available for testing with HIV DNA in vitro and for HIV-infected human cells consist of three distinct parts:

a) the "carrier": it is a small oligonucleotide (i.e. a short piece of single-stranded DNA) which consists of 15–20 nucleotides. The nucleotide sequences are programmed to recognize and interact with a single DNA sequence of a selected HIV target gene. Since the specificity of this reaction is very high (1:20,000–30,000; see above) the interaction of the carrier should be restricted to the selected HIV DNA target without interference with cellular genes. The reaction of the oligonucleotide with the target sequence should lead under physiological conditions to the formation of a noncovalent triple helix. This interaction leads to a blockage of the expression of the target gene; since this block is, however, limited in time we link the oligonucleotide to a "warhead" which inactivates the target gene. To render the oligonucleotides (carriers) resistant to intracellular exo- and endonucleases the oligonucleotides used in this project are produced in an automated DNA-synthesizer, using different nucleotide analogs. A further protection against intracellular degradation of the carrier has recently been achieved in our laboratories by the phosphorylation of the 5'-and/or the 3'-ends of the oligonucleotide chains (FIG. 1). Again this reaction is now carried out in an automated DNA synthesizer. For further preclinical and more so for future clinical studies it is of importance that the carriers (and thus the "bombs") can now be produced in rather large amounts using the automated procedures presently available.

b) The "warhead": It corresponds to the active compound of the "bomb". One type of warhead now available is derived from a variety of naturally occurring or synthetic anticancer antibiotics all of which contain a 3-ene-1,5 diyne bridge (FIG. 3). This bridge is under high tension; upon interaction with double-stranded DNA this structure rearranges into a highly reactive biradical which induces in the target DNA sequence a double strand break. Alternative types of "warheads" have recently been developed which covalently and irreversibly bind to the target DNA and in this way lead to the inactivation of the target gene.

c. The "linker" allows to covalently attach organic compounds to the 3'-and/or 5'-termini of oligonucleotides. FIG. 4 shows an oligonucleotide (directed against the early gene of the SV40 tumor virus) to which an intercalating acridine derivative was fixed to both termini. The same chemical technique has now been applied to link different "warheads" to specifically programmed oligonucleotides.

MOLECULAR AND BIOLOGICAL STUDIES WITH HIV

HIV isolates show relatively frequent sequence variations over the entire genome. The efficiency of triple helix formation with oligonucleotides of different size and with one or two mismatches needs to be tested by in vitro experiments.

a. Potential target sequences for triple helix formation

The following discussion is based on the nucleotide sequence and numbering of the HIV-1 proviral genome (EMBL Gene Bank NREHTLV3, accession number X01762).

Two possible target sequences are as follows: The first one is located in the polymerase gene and has a homopurine stretch of 17 bp (bp—base pairs) or alternatively has 23 bp containing one T (SEQ ID NO: 1):

$$_{2698}AGAAATGGAAAAGGAAGGGAAAA_{2720}$$

The second possible sequence is located in the env gene. It consists of 17 bp with two T residues (SEQ ID NO: 2):

$$_{7051}AGAAGAAGAGGTAGTAA_{7067}$$

These two target sequences are within conserved regions and also within PCR-amplifiable fragments for which the primers and amplification conditions are already available and which are therefore particularly suited for the in vitro experiments described below. The fragment from the polymerase gene has about 760 bp and the fragment from the env gene about 400 bp.

In the HIV-1 genome there are however other potential target sequences which may be targeted:

| Homopurine stretches: | |
|---|---|
| with 17 bp occur 1 times: | |
| GGAAAAGGAAGGGAAAA | (SEQ ID NO: 23) |
| with 16 bp occur 3 times: | |
| AGGGGGAAAGAAAAAA | (SEQ ID NO: 20) |
| $_{4817}$AAAAGAAAAGGGGGGA$_{4832}$ | (SEQ ID NO: 21) |
| $_{9098}$AAAAGAAAAGGGGGGA$_{9113}$ | (SEQ ID NO: 22) |
| with 15 bp occur 2 times: | |
| AGAGAGAAAAAAGAG | (SEQ ID NO: 18) |
| AAGAGGAGGAGGAGG | (SEQ ID NO: 19) |
| with 14 bp occur 3 times: | |
| AAAAAAGGAAAAGG | (SEQ ID NO: 15) |
| GGAGGAAAAAGAGA | (SEQ ID NO: 16) |
| GGAGAAAGGAGAGA | (SEQ ID NO: 17) |
| with 13 bp occur 1 times: | |
| AAAAAAGAAAAAA | (SEQ ID NO: 14) |
| with 12 bp occur 2 times: | |
| AGGAGAAAGAGA | (SEQ ID NO: 12) |
| AGAAGAAGAAGG | (SEQ ID NO: 13) |
| Purine rich sequences containing 1 pyrimidine: | |
| with 24 bp occurs 1 times: | |
| AGAAGAAGAAGGTGGAGAGAGAGA | (SEQ ID NO: 39) |
| with 21 bp occurs 1 times: | |
| GGAGAAAGGAGAGATAAAAAA | (SEQ ID NO: 38) |
| with 20 bp occur 1 times: | |
| GAAGGAATAGAAGAAGAAGG | (SEQ ID NO: 36) |
| with 19 bp occur 1 times: | |
| AAGAGGAGGAGGAGGTGGG | (SEQ ID NO: 37) |
| with 17 bp occur 4 times: | |
| AGAAGGAGAGAGATGGG | (SEQ ID NO: 32) |
| AATAAAAAAGGAAAAGG | (SEQ ID NO: 33) |
| AAGAAGAAAAGCAAAGA | (SEQ ID NO: 34) |
| GCAGAGAGAAAAAAGAG | (SEQ ID NO: 35) |
| with 16 bp occur 3 times: | |
| GAAAGCGAAAGGGAAA | (SEQ ID NO: 29) |
| AAAAGTAAGAAAAAAG | (SEQ ID NO: 30) |
| GAGAGTGAAGGAGAAA | (SEQ ID NO: 31) |

-continued with 15 bp occur 3 times:

| | |
|---|---|
| AAGATAGAGGAAGAG | (SEQ ID NO: 26) |
| AGAGGAAGAGCAAAA | (SEQ ID NO: 27) |
| AGGAAGAAGCGGAGA | (SEQ ID NO: 28) | with 14 bp occur 2 times:

| | |
|---|---|
| GGCAGAAGAAGAGG | (SEQ ID NO: 24) |
| AAGAAAAGAATGAA | (SEQ ID NO: 25) |

Purine rich sequences containing 2 pyrimidine:

with 32 bp occur 1 times:
| | |
|---|---|
| GAAGGAATAGAAGAAGAAGGTGGAGAGAGAGA | (SEQ ID NO: 41) | with 20 bp occur 1 times:
| | |
|---|---|
| AAGAAAAGAATGAACAAGAA | (SEQ ID NO: 40) | b. In vitro experiments with PCR-amplified DNA fragments

Specificity and stability of in vitro triple helix formation at different pH, temperatures and DNA/oligonucleotide ratios is tested with labeled oligonucleotides and PCR-amplified HIV DNA fragments by band shift assays.

Specificity and efficiency of double-stranded DNA cleavage by the "biological bombs" is assayed with labeled PCR fragments and gel electrophoresis.

c. Experiments with HIV-infected human cells in culture

For these studies MT-2 cells (a human T cell leukemia cell line showing maximal cytopathic effects upon infection with HIV-1) is used [Harada et al. Science 229,563–566, 1985). After infection with HIV-1 (AZT resistant, lot 5 G691-2) and treatment with various concentrations of the "biological bombs" the supernatant medium is analyzed regularly for production of p24 antigen which reflects adequately virus production. Other experiments are performed with labeled "bombs" to determine the extent of penetration into uninfected and HIV-1-infected cells and their intracellular stability and fate.

The compounds and methods described herein offer several advantages. First, the phosphorylating agents can be easily attached to a solid support. Second, the phosphorylating agents are well suited to the phosphoroamidite methods—one of the most widely used methods in synthesizing an oligonucleotide on a DNA synthesizer. Third, since the phosphorylating agents are stable and can withstand being run on an automatic DNA synthesizer, bulk quantities can be produced. Fourth, the phosphorylating agents phosphorylate both the 3' and 5' end of an oligonucleotide easily on a DNA synthesizer Further, the 3',5'-diphosphate oligonucleotide are produced in high yields. Finally, once a 3',5'-diphosphate oligonucleotide is produced, an oligonucleotide conjugate (oligonucleotide linked to a warhead) may be synthesized readily.

Experimental Details

The synthesis begins with mono-(4,4'-dimethoxy)tritylation of $S^1,S^2$-bis(2-hydroxyethyl)disulfide (1). The mono-substituted product, $S^1$-2-O-(4,4'-dimethoxytrityl)oxyethyl-$S^2$-(2-hydroxyethyl) disulfide (2) is then converted into the phosphoroamidite, $S^1$-[2-(4,4'-dimethoxytrityl)oxy]ethyl-$S^2$-[N-diisopropylamido-O-(2 -cyanoethyl)phosphityl]ethyldisulfide (3) by treatment with chloro-N,N-diisopropyl-(2-cyanoethyl)phosphoroamidite in methylene chloride in the presence of diisopropylethylamine.

Alternatively, bis (2-hydroxyethyl) sulfone (4) is converted into [2-(4,4,-dimethoxy)trityloxy]ethyl-(2hydroxyethyl)sulfone (5), which is further converted into [2-(4,4'-dimethoxytrityl)oxy]ethyl-[N-diisopropylamido-O-(2-cyanoethyl) phosphityl]ethyldisulfide (6).

Compound 2 or 5 is condensed with the activated ester of controlled pore glass (CPG) derivative (7). The protected product 8 is then placed in a reaction column of an automated DNA synthesizer.

Using a DNA synthesizer, employing the phosphoroamidite procedure, the following steps are performed:

(1) Compound 8 is deprotected to produce compound 9.
(2) Compound 9 is then condensed with a suitably protected phosphoroamidite nucleotide monomer to give 10.
(3) Compound 10 is deprotected to produce 12.
(4) During the chain elongation process, llustrated in FIG. 1, steps 2 and 3 are repeated until the desired oligonucleotide (compound 13 or 14) is produced.

Compound 14, the deprotected oligonucleotide attached to the CPG solid support derivative, is treated with compound 3 or to give the protected oligonucleotide precursor 15. Compound 15 undergoes oxidation followed by ammonium hydroxide treatment to produces the desired product (3',5'-diphosphate oligonucleotide: Formula I in FIG. 1).

Figure 2:
FIG. 2: A synthetic scheme for the synthesis of an oligonucleotide having warheads on both ends of the chain. The substituent R may be one of the warheads listed in FIG. 3, Compounds A–E.
Figure 2:
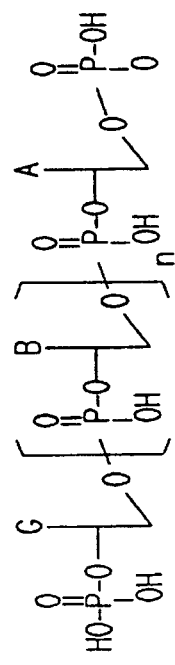
Figure 2:
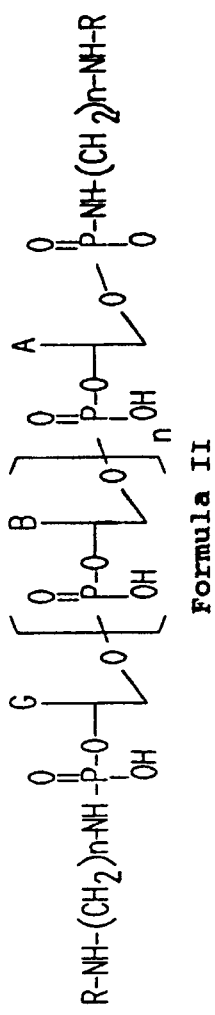
Figure 3A:
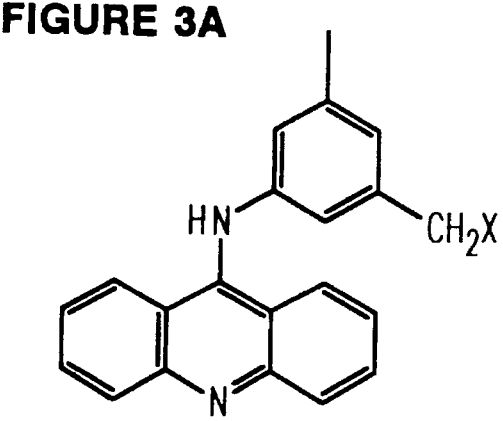
FIG. 3A–3E: Various chemical warheads that can be linked to an oligonucleotide. Substituents: X is —O—CO— NH—Y; Y is —H, $C_1$–$C_{10}$ alkyl; and X' is —H, —OH, —$OCH_3$; and R is —H, $C_1$–$C_{10}$ alkyl which may independently be straight chain or branched, substituted or unsubstituted. (A) Compound A is an acridine derivative and is an intercalator. (B) Compound B is Mytomycin C, and is a cross linker. (C) Compound C a crosslinking intercalator developed in our laboratories. It intercalates into doublestranded DNA, binds covalently to both strands and thus irreversibly inactivates the target gene. (D) Compound D is an enediyne that cleaves double-stranded DNA by producing free radicals. (E) Compound E is a iron chelate that cleaves a double-stranded DNA by producing a free radical.
Figure 3B:
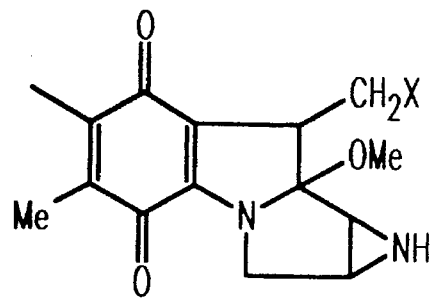
Figure 3C:
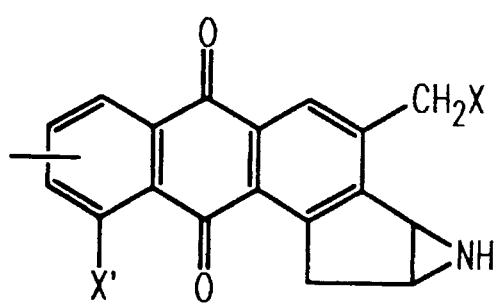
Figure 3D:
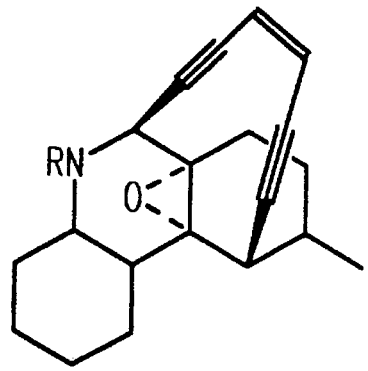
Figure 3E:
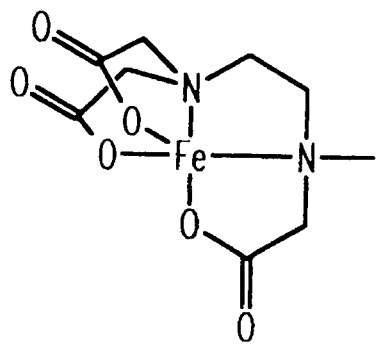

Oligonucleotides of Formula I (FIG. 1) may be readily attached to any alkyl or aromatic amine including intercalating agents to give oligonucleotide conjugates of general Formula II (See FIG. 2). The synthesis of oligonucleotide conjugates using Formula I oligonucleotides is illustrated in FIG. 2.

EXAMPLE 1

$S^1$-(4,4'-Dimethoxytrityl)oxyethyl-$S^2$-(2-hydroxyethyl) disulfide (2)

To a mixture of $S^1$, $S^2$-di(2-hydroxyethyl)disulfide (1) (5 g, 32 mmole), 4,4'-dimethoxytrityl chloride (10.53 g, 31 mmole), 165 mg of p-dimethylaminopyridine and 6.5 ml of triethylamine in 250 ml of pyridine was stirred at room temperature for 18 hours. The mixture was concentrated to dryness in vacuo, and the residue was dissolved in methylene chloride (250 ml), washed twice with water (each 200 ml), dried over sodium sulfate, and the concentrated in vacuo. The residue was dissolved in a minimal amount of methylene chloride, and the solution placed on the top of a column of silica gel and eluted with 10%, 20% and 40% of EtOAc/hexane. The pure 2 was obtained as a heavy syrup (8 gm, 57%).

EXAMPLE 2

2-(4,4,-Dimethoxytrityl)oxyethyl-2'-hydroxyethylsulfone(5)

Water was removed from bis(2-hydroxyethyl)sulfone (65% in water, 14 gm, −9.1 gm dry weight, 59 mmole) by distillation under reduced pressure. The residue was coevaporated three times with dry pyridine. The tritylation condition was identical to preparation of compound 2 with same rate and scale. The final reaction mixture was evaporated to dryness, and the residue was dissolved in ethyl acetate. Insoluble white precipitates were removed by filtration. The filtrate was concentrated to about 20 ml, and the solution was placed on a column of silica gel. The column was eluted with EtOAc/hexane to give 12 gm of 5 in 46% yield.

EXAMPLE 3

[2-(4,4'-dimethoxytrityl)oxy]ethyl-[N-diisopropylamido-O-(2-cyanoethyl)phosphityl]-ethylsulfone. (Phosphoroamidite reagent 6).

Compound 5 (4 gm, 10 mmole), after coevaporation with 10% dry pyridine in dry methylene chloride (twice distilled over phosphorus pentoxide), was dissolved in a mixture of diisopropylethylamine (12 ml) (dried over calcium hydride) and dry methylene chloride (30 ml). To the stirred mixture under argon atmosphere was added 4 ml of chloro-N,N'-diisopropyl-2'-cyanoethyl phosphoramidite using a syringe. The reaction progress was monitored by thin layer chromatography. After the reaction was completed, the excess phosphitylating reagent was quenched with methanol. The mixture was diluted with ethyl acetate containing 5% of triethyl amine, and washed with 10% sodium bicarbonate, water, dried and evaporated. The pure product 6 was isolated by silica gel column chromatography eluted with hexanes:EtOAC:Et$_3$N (75:20:5) to give 4.5 gm in 70 % yield.

By the same procedure but using 2 instead of 5, S$^1$-[2-(4,4'-dimethoxytrityl) oxy]ethyl-S$^2$-[N-diisopropylamido-O-(2cyanoethyl) phosphityl]ethyldisulfide (phosphoroamidite reagent 3) was obtained.

EXAMPLE 4

S$^1$-[2-(4,4'-dimethoxyltrityl)oxyethyl]-S$^2$-(2'-oxyethyl) disulfide-2'-O-succinylated controlled pore glass (CPG ) support (8, Z=—S—S—)

Controlled pore glass (500Å) (CPG-500Å) (3 g) was coevaporated twice with pyridine (dried over CaH$_2$ and distilled) before use. A mixture of CPG, succinic anhydride (500 mg) and N-methylimidazole (1 ml) in 10 ml of dry pyridine was gently shaken overnight in a mechanic shaker. The liquid was removed as much as possible by decantation followed by suction with a pipette. The unreacted amino groups of CPG was capped with 2 ml of chloro trimethylsilane in 8 ml of fresh dry pyridine. After being shaken for 5 hours, the mixture was filtrated, and the CPG was washed with pyridine, ethanol and ethyl ether (10 ml each). The dried CPG (1.5 gm) was linked with tritylated alcohol 2 (500 mg each) by shaking with 2,4,6-triisopropylbenzenesulfonyl chloride(500 mg) and N-methylimidazol (0.6 ml) in 10 ml of dry pyridine for 18 hours. The CPG derivative 8, wherein Z=—S—S—, was obtained by filtration, washed with pyridine, EtOH and ether and dried with P$_2$O$_5$ in vacuo at room temperature.

In a similar procedure using 5 instead of 2, [2-(4,4'-dimethoxytrityl) oxy]ethyl-[2'-oxyethyl]-1'-succinylated controlled pore glass (8, Z=SO$_2$) was obtained.

The loading capacity of these 3'-phosphate compounds on CPGs were established by standard dimethoxytrityl analysis. The detritylation of 8 was carried out by 70% hydroperchloric acid in methanol and measured at UV/VIS absorbance at 498 nm. The usual loading for the preparation is around 30–40 μM/gm which is comparable to the loading for normal deoxynucleoside-linked CPG.

EXAMPLE 5

Oligonucleotide bearing protected phosphate groups on both the C-3' and C-5' ends (15) on a synthesizer.

The CPG derivative 9 was placed in a reaction column of a automatic DNA synthesizer. Without modification of any default parameters and program settings in an automatic DNA synthesizer, compound 13 or 14 was produced by regular elongation reactions. The column was then treated with compound 3 or 6 to give a regular oligonucleotide bearing protected phosphate groups on both the C-3' and C-5' ends (15).

EXAMPLE 6

Oligonucleotide bearing phosphate groups on both the C-3' and C-5 ' ends (Formula I; FIG. 1)

Upon oxidation of the protected oligomer attached to the CPG support (15), followed by treatment with 40% aqueous ammonia at 60° C. overnight, an oligonucleotide of Formula I was obtained. This oligomer may be purified by high pressure liquid chromatography, but may be used directly in the phosphate group modification to produce oligonucleotide conjugates.

EXAMPLE 7

An oligonucleotide bearing anticancer intercalating agents on both the C-3' and C-5' ends through phosphoroamidate linkages (Formula II; FIG. 2)

Seventy milligrams of crude oligonucleotide of Formula I 20 mg of the amino acridine was mixed with 25 mg of triphenylphosphine and 15 mg of 2,2'-dipyridyl disulfide in 5 ml of DMF. The reaction mixture was shaken for 5hr and then added 500 ul of water. After being shaken in a shaker overnight, the solid was separated from DMF by centrifugation, and then washed with absolute ethanol twice, centrifuged and dried in speedvac to give a yellow powder. The dicrosslinked drug-oligomer was purified by reverse phase HPLC. The mobile phase gradient was 25% of 70% of acetonitrile in water for 50 minutes to 100% in 0.1M TEAB(triethylamonium bicarbonate) in C$_{18}$ reverse phase column. The unreacted oligomers had retention time 5.8 min and dicrosslinked oligomer at 14.5 min and unreacted amino acridine at 27 min The UV/VIS spectra of compound had $\lambda_{max}$ at 260 nm and 400 um.

The aminoacridine (A) is prepared as follows (FIG. 2):

9-(4'-Mesyloxyethyl)anilinoacridine (C)

To a mixture of 9-(4'-Hydroxymethyl)anilinoacridine (B) (4.00 gm, 28.8 mmole) and triethylamine (4 ml)-in 150 ml of methylene chloride was added dropwise a solution of mesyl chloride (4 ml) in methylene chloride (50 ml) at ambient temperature. The reaction was monitored by thin layer chromatography. After completion of reaction, the mixture was diluted with an additional methylene chloride (150 ml), and washed with 2N hydrochloric acid once, brine twice, dried over sodium sulfate, and then concentrated in vacuo. The residue was dissolved in 25 ml of chloroform. To the solution was added gradually added 150 ml of ethyl ether to form an amphibious tar like precipitate. The solvent was removed by decantation, and the precipitate washed with ethyl ether, and dried in vacuo to give crude C which is used directly in next step.

9-(4'-azidoethyl)anilinoacridine(D)

To a mixture of crude acridine mesylate C (4.5 gm,~11 mmole) and lithium azide (5 gm, 0.1 mole) in 50 ml of dimethylformamide was stirred at room temperature for 18 hours. The mixture was concentrated in vacuo and the residue was taken up into ether. The ether solution was washed twice with brine, dried, and then concentrated. Crystallization of the product occurred during concentration. The crystalline D was collected by filtration and washed with a 1:1 ether/n-hexane mixture to give 1.42 gm of D (37% yield overall from B).

9-(4'-aminoethyl)anilinoacridine (E)

The azido compound D (409 mg, 1.22 mole) was treated with triphenylphosphine (420 mg, 1.6 mmole) in 10 ml of pyridine at ambient temperature with stirring for 4 hours. One milliliter of concentrated ammonia solution was added, and the mixture was kept at room temperature 3 more hours. After evaporation of the solvent, the residue was chromatographed on a silica gel column using methylene chloride-methanol (20:1 and 10:1). The desired amino compound E was crystallized from methanol-ether to give 70 mg (19% yield) of pure product.

Homo- and Hetero-oligomers (Formula I or II compounds):

Oligomers containing fluorinated sugar nucleosides may be prepared on our oligonucleotide synthesizer. The parameters need to be optimized on the synthesizer for the synthesis of oligomers containing various purine and pyrimidine 2'-fluorinated nucleotides. The sequences of interest that may be synthesized are listed in Table 1. Most of the sequences listed are undecamers which may be used to study duplex and exonuclease stabilities. Seven sequences are preferred to be synthesized (Table 1, numbered). The first sequence is the oligonucleotide fragment complementary to the reiterated terminal sequences of Rous Sarcoma virus. Zamecnik and Stephenson [Zamecnik, 1978; 1979] demonstrated that this sequence inhibits the replication of the intact virus. The second and third oligomers are analogues of dodecamers, dTTCCTCCTGCGG (SEQ ID NO: 3) and dCCCGGCCTGCGA (SEQ ID NO: 4), respectively, which have sequences complementary to six bases on either side of the splice acceptor junction of HSV-1 and HSV-2 immediate early (IE) mRNA 4; HSV-1 IE mRNA 4:

sequence of HSV-1 of the same fragment, and found their oligomer inhibited viral (but not cellular protein) synthesis, and decreased splicing of IE pre-mRNAs 4 and 5 [Smith, 1986]. IE genes play a regulatory role in HSV replication [Everett, 1987]. We may also synthesize the complementary base sequence of part of two oncogenes H-ras (#4 and #5 of the list, Table 1). Oligomers #6 and #7 have the sequences complementary to initiation codon and the 12th amino acid codon regions of c-Ha-ras oncogene.

The same sequences are synthesized, but with all or part of nucleotides displaced by 2'-fluorinated -nucleotides, to compare the activity with their respective unmodified sequences. The synthesis of these oligomers is performed by the same procedure used for the standard synthesis of oligomers.

It should be noted that the H-phosphonate procedure has an added advantage for oligomer modification: it may be possible to introduce substituted phosphoramidate at any specific phosphorus atom by oxidation of internucleotide H-phosphonate with charbon tetrachloride in the presence of primary amine in pyridine [Letsinger, 1989; Agrawal, 1990]. Recently, a rather simple method of the site-specific incorporation of a thiol tether has been reported [Fidanza, 1992] using the H-phosphonate intermediates.

Large amounts (20–22 mg) of oligomers phosphorylated on both ends of the chain by the method shown in FIG. 1 (Formula I) have been synthesized using the phosphoroamidite procedure. LCAA-CPG (LCAA—long chain alkylamine) was converted into 7 by treatment with succinic anhydride, followed by p-nitrophenyl ester formation. The active ester 7 was converted into 8, which was detritylated to give 9. Coupling 9 with a suitable protected nucleotide phosphoroamidite in the presence of tetrazole gave 10, which was oxidized to 11. After detritylation of 11 to 12, a suitable protected nucleotide phosphoroamidite was coupled again to the 5'-end of the nucleotide attached to the solid support 12. The oxidation, detritylation and coupling cycles were repeated until the desired sequence 13 is completed. Detritylation of 13 afforded 14, from which Formula I was obtained in good yield by coupling with 14 to 3 or 6, followed by oxidation and deprotection. By modification of this method, oligomer-intercalator conjugate in FIG. 4 was synthesized. The H-phosphonate procedure or phosphoroamidite procedure may be used depending upon the nature of oligomers or conjugates.

| HSV-1 IE mRNA 4: INTRON EXON | |
|---|---|
| 5' CGTGCCTTCCCGCAG GAGGAACGTCCTCGT 3' | (SEQ ID NO: 42) |
| 3' GGCGTC CTCCTT 5' | (SEQ ID NO: 3) |
| HSV-2 IE mRNA 4: INTRON EXON | |
| 5' CGCGCTTTCTCGCAG GCCGGGCGCCGCCTT 3' | (SEQ ID NO: 43) |
| 3' AGCGTC CGGCCC 5' | (SEQ ID NO: 4) | respectively. Kulka et al. [Kulka, 1989] synthesized oligo-(nucleoside methylphosphonate)s of the antisense base

TABLE 1

Oligonucleotide sequences for basic studies.

| Oligomer | N | Oligomer | N | Oligomer | N | Oligomer | N |
|---|---|---|---|---|---|---|---|
| d(N)$_{11}$ | F-ara-T | | | | | | |
| | F-ara-C | d(A-N)$_5$ | F-ara-A | d(C-N)$_5$ | F-ara-C | d(N-T$_{10}$) | F-ara-T |
| | F-ara-U | d(A$_5$-N-A$_5$) | F-ara-A | d(C$_5$-N-C$_5$) | F-ara-C | d(T$_{10}$-N) | F-ara-T |
| | F-ara-A | d(A$_4$-N$_2$-A$_4$) | F-ara-A | d(C$_4$-N$_2$-C$_4$) | F-ara-C | d(N-T$_9$-N) | F-ara-T |
| | F-ara-G | d(A$_4$-N$_3$-A$_4$) | F-ara-A | d(C$_4$-N$_3$-C$_4$) | F-ara-C | d(N$_2$-T$_9$) | F-ara-T |
| | F-ara-H | d(N-A$_{10}$) | F-ara-A | d(N-C$_{10}$) | F-ara-C | d(T$_9$-M$_2$) | F-ara-T |
| | | d(T-N)$_5$ | F-ara-A | d(G-N)$_5$ | F-ara-C | | |
| d(T-N)$_5$ | F-ara-U | | | | | | |
| d(T$_4$-N$_2$-T$_4$) | F-ara-U | d(G-N)$_5$ | F-ara-G | 1 d(AATGGTAAAATGG) (SEQ ID NO: 5) | | | |
| d(T$_4$-N$_3$-T$_4$) | F-ara-U | d(G$_5$-N-G$_5$) | F-ara-G | 2 d(TTCCTCCTGCGG) (SEQ ID NO: 6) | | | |
| d(N-T$_{10}$) | F-ara-U | d(G$_4$-N$_2$-G$_4$) | F-ara-G | 3 d(CCCGGCCTGCGA) (SEQ ID NO: 7) | | | |
| d(T$_{10}$-N) | F-ara-U | d(G$_4$-N$_3$-G$_4$) | F-ara-G | 4 d(CGGTGGCGCTGCGCAAGGTAAAACGC) (SEQ ID NO: 8) | | | |
| d(N-T$_9$-N) | F-ara-U | d(N-G$_{10}$) | F-ara-G | 5 d(ACACGAATTTTATTTAATAC) (SEQ ID NO: 9) | | | |
| d(N$_2$-T$_9$) | F-ara-U | d(N-G)$_5$ | F-ara-G | 6 d(ATGACTGAATA) (SEQ ID NO: 10) | | | |
| d(T$_9$-M$_2$) | F-ara-U | | | 7 d(CTTAGGAC) | | | |

Synthesis of Oligomers which are attached to intercalating agent(s) at terminal(s) (Formula II):

A number of methods are available to link reactive agents to the 3' [Chou, 1987; Asseline, 1986] or 5' [Vlassov, 1986; Boutorin, 1984; Chu, 1985; Dreyer, 1985; Asseline, 1988; Pankiewicz, 1992] end of oligomers. Methods are also available to modify both ends of oligomers with the same [Asseline, 1988; Thung, 1987] or different groups [Le Doan, 1987; Biodot-Forget, 1988]. The method of Kutyavin et al. [Kutyavin, 1988] may be used by activating the terminal phosphate(s) with N,N-dimethylaminopyridine or its N-oxide in the presence of triphenylphosphine and bis(2-pyridyl)disulfide, followed by treatment with the primary amines. As a model, we have synthesized the conjugate in FIG. 4, which contains 39 nucleotides of the coding sequence of Exon 1 of the SV40 T-antigen. The purine-rich H-ras gene sequence d(GGCGCTGCGCAAGGTAAAA) (SEQ ID NO: 11) is used, since this single-stranded oligodeoxynucleotide sequence (D) is expected to form a Pu+Pu–Py triplex with the corresponding double-stranded DNA (DD) in a D+DD fashion, and there are many G-C pairs near the both 3' and 5' ends of the targeted sequence. The chemistry for linking has been well established, and we may use the procedure shown in FIG. 2 which we developed and used it in the synthesis of the conjugate in FIG. 4. (Very recently, a similar chemistry is reported subsequent to applicants invention [Kumar, 1993]. The agents that may be linked to the oligomer are listed in FIG. 3. We have linked our intercalating cross-linker (FIG. 3, compound C) to an oligomer as our major target. We have also synthesized conjugates with an acridine intercalator (FIG. 3, compound A) cross-linker mitomycin C (MC) (FIG. 3, compound B) as controls. Compound C (FIG. 3) may be delivered to the targeted sequence of the gene and the intercalator portion cross-link to the both strands of DNA locking permanently the particular targeted section of the gene. This type of "antigene" approach has little been explored. The efficacy of such a conjugate may be examined by comparison of the long term and selective anticancer activity of two other types of conjugates (compound A and B in FIG. 3). Compound A may be less effective, since it does not permanently damage the targeted portion of the gene. The MC-conjugate may be less selective and less effective, since the MC portion of the conjugate can cross-link to the two bases of the same (one) strand, in which case the repair mechanism can operate. Mitomycin C cross-links to the GC pair [Tomasz, 1987; Tomasz, 1981]. Therefore, the presence of such pairs near the end of targeted DD strands is extremely important.

It is obvious from FIG. 5, that Hoogsteen strand should be either homopurine or homopyrimidine, because the angle of glycosyl bond is quite different for pyrimidine (the sugar is in the 9 o'clock direction in FIG. 5) than from purine (the sugar residue resides at the 1 o'clock angle). Therefore, presence of a few pyrimidine bases should twist the purine-rich Hoogsteen strand and destabilize the triple helix. In order to avoid this, the five pyrimidine nucleosides may be replaced in the in the sequence with methyl 2'deoxy-2-fluoro-D-arabinofuranoside or 3-fluoro-4-hydroxyfurfuryl alcohol, and the triplex stability with the triplex consisting of unmodified sequences may be compared. Although methyl 2-deoxy-2-fluoro-β-D-arabinofuranoside or 3-fluoro-4-hydroxy-tetrahydrofurfuryl alcohol has never been used for such purposes, a similar (but not exactly the same) concept has already been developed by others in the triplex area. For example, 4-hydroxy-tetrahydrofurfuryl alcohol has been used as a cross-over or switchback linker in 3', 3'- or 5',5'-linked Hoogsteen oligomers for triplex formations [Horne, 1990; Luebke, 1992; Froehler, 1992]. An additional advantage of this modified Hoogsteen strand is that there is no cytidine, and consequently, it does not require acidic conditions to protonate the cytosine base to form a triplex.

The chemistry for the synthesis of our targeted conjugates has been well established, and we have already prepared such a conjugate as in FIG. 4, using the procedure shown in FIG. 1 and 2. The chemistry is available to modify both ends of the oligonucleotide with the same or different agents. It is, however, necessary to find the optimal chain-length especially for crosslinking agents to find a CpG or GpC sequence and most easily form interstrand cross-links at two diagonally opposed dG residues. Computer modeling {Quanta} and CHARMm .calculations are used. The recent report describing the method of incorporation of a thiol tether will be useful not only in the oligomer modifications, but also in rhodamine-drug conjugate synthesis. The thiol tether approach is used to adjust the length of the chain connecting between the oligomer and intercalating agent [Fidenza, 1992]. Compounds in FIG. 3 may be derivatized as shown in FIG. 2 before being linked to the oligomer.

References

1) Agrawal, S.; Tang, J. Y. Tetrahedron Lett., 1990, 31, 1543–1546.
2) Asseline, U.; Thuong, N. T. Nucleosides Nucleotides, 1988, 7, 431–445.
3) Asseline, U.; Thung, N. T. Tetrahedron Lett., 1986, 30, 2521–2524.
4) Beal P. A. and Dervan P. B. 1991. Second structure motif for recognition of DNA by oligonucleotide-directed triple helix formation. Science 251, 1360–1363.

5) Boidot-Forget, M.; Chassignol, M.; Takasugi, M.; Thuong, N. T.; Helene, C. Site-specific cleavage of single-stranded and double-stranded DNA sequences by oligodeoxyribonucleotides covalently linked to an intercalating agent and an EDTA-Fe chelate. Gene, 1988, 72, 361–371.

6) Boutorin, A. S., Vlassov, V. V., Kazakov, S. A., Kutiavin, I. V., Podyminogin, M. A. Complementary addressed reagents carrying EDTAFe(II) groups for directed cleavage of single-stranded nucleic acids. FEBS Lett., 1984, 172, 43–46.

7) Chou, T. C.; Kong, X. B.; Fanucchi, M. P.; Cheng, Y. C.; Takahashi, K.; Watanabe, K. A.; Fox, J. J. Antimicrob. Agents Chemotherap., 1987, 31, 1355–1358.

8) Chu, B. C. F., Orgel, L. E. Nonenzymatic sequence-specific cleavage of single-stranded DNA. Proc. Nat. Acad. Sci., USA, 1985, 82, 963–967.

9) Dreyer, G. B., Dervan, P. B. Sequence-specific cleavage of single-stranded DNA: oligo-deoxynucleotide-EDTA.Fe(II). Proc. Nat. Acad. Sci., USA, 1985, 82, 968–972.

10) Everett, R. D. The regulation of transcription of viral and cellular genes by herpesvirus immediate-early gene products. Anticancer Res., 1987, 7,589–604.

11) Felder, E.; Schwyzer, R.; Charubala, R.; Pfleiderer, W.; Schultz, B. Tetrahedron Lett., 1984, 25, 3967.

12) Fidanza, J. A.; McLaughlin, L. W. Use of a thiol tether for the site-specific attachment of receptor group to DNA. J. Org. Chem., 1992, 57, 2340–2346.

13) Froehler, B. C.; Terhorst, T.; Shaw, J. P.; McCurdy, S. N. Triple-helix formation in cooperative binding by oligodeoxynucleotides with a 3'-3'-internucleotide junction. Biochemistry, 1992, 31, 1603–1609.

14) Geisow M. J. 1991. DNA-based drugs, diagnostics and devices. TIBITECH 9, 33–338.

15) Gough, G. R.; Brunden, K. J.; Gilham, P. T. Tetrahedron Lett., 1983, 24,5317.

16) Helene C. and Le Doan T. 1991. Oligonucleotides: problems and frontiers of practical applications. TIBITECH 9, 341–342.

17) Kulka, M.; Smith, C. C.; Aurelian, L.; Fishelevich, R.; Meade, K.; Miller, P.; Ts'o, P. O. P. Site specificity of the inhibitory effects of oligo(nucleoside methylphosphonate)s. Proc. Nat. Acad. Sci., USA, 1989, 86, 6868–6872.

18) Kumar, A. A new solid-phase method for the synthesis of oligonucleotides with terminal 3'-phosphate. Nucleosides Nucleotides, 1993, 12, 441–447.

19) Kutyavin, I. V.; Podyminogin, M. A.; Bazhina, Y. N.; Fedorova, O. S.; Knorre, D. G.; Levina, A. S.; Mamaev, S. V.; Zarytova, V. F. FEBS Lett., 1988, 238, 35–38.

20) Le Doan, T.; Perroualt, L.; Chassignol, M.; Thuong, N.T.; Helene, C. Sequence-targeted chemical modifications of nucleic acids by complementary oligonucleotides covalently linked to porphyrins. Nucleic Acids Res., 1987, 15, 8643–8659.

21) Letsinger, R. L.; Guangrong, Z.; Sun, D. K.; Ikeuchi, T.; Sarin, P. Proc. Nat. Acad. Sci., USA, 1989, 86, 6553–6556.

22) Luebke, K. J.; Dervan, P. Nonenzymatic ligation of double-helical DNA by alternate-strand triple helix formation. Nucleic Acids Res., 1992, 20, 3005–3009.

23) Marks, P. A.; Turler, M.; Weil, R. Precancerous lesions: a multidisciplinary approach, Challenges of Modern Medicine, 1993.

24) Maniatis, T.; Fritsch, E. F.; Sambrook, J. (1982) Molecular Cloning: A Laboratory Manual (Cold Spring Harbor Laboratory, Cold Spring Harbor, N.Y.).

25) Moser H. E. and Dervan P. B. 1987. Sequence specific cleavage of double helical DNA by triple helix formation. Science 238, 645–650. Horne, D. A., Dervan, P. B. Recognition of mixed-sequence duplex DNA by alternate-strand triple-helix formation. J. Am. Chem. Soc., 1990, 112, 2435–2437.

26) Pankiewicz, K. W.; Krzeminski, J.; Watanabe, K. A. A new synthesis of 9-(2-deoxy-2-fluoro-β-D-arabinofuranosyl)-guanine. Abstract CARB 45, 203rd ACS National meeting, San Francisco, April, 1992.

27) Stephenson, M. L., Zamecnik, P. C. Inhibition of Rous sarcoma viral RNA translation by a specific oligodeoxynucleotide. Proc. Nat. Acad. Sci. USA, 1979, 75, 285–288.

28) Smith, C. C.; Aurelian, L.; Reddy, M. P.; Miller, ; P. S., Ts'o, P. O. P. Antiviral effect of an oligo(nucleoside methylphosphonate) complementary to the splice junction of herpes simplex virus type 1 immediate-early pre-mRNAs 4 and 5. Proc. Nat. Acad. Sci., USA, 1986, 83, 2787–2791.

29) Stein, C. A.; Cheng, Y. C. Antisense Oligonucleotides as Therapeutic Agents—Is the Bullet Really Magical?, Science, 1993, 261, 1004.

30) Strobel S. A. and Dervan P. B. 1990. Site-specific cleavage of a yeast chromosome by oligonucleotide-directed triple helix formation. Science 249, 3–5.

31) Thung, N. T.; Chassignol, M. Tetrahedron Lett., 1987, 28, 4157–4160.

32) Tomasz, M.; Lipman, R.; Chowdary, D.; Pawlak, J.; Verdine, G. L.; Nakanishi, K. Isolation and structure of a covalent cross-link adduct between mitomycin C and DNA. Science, 1987, 235, 1204–1208.

33) Tomasz, M.; Lipman, R. Reductiove metabolism and alkylating activity of mitomycin C induced by rat liver microsomes. Biochemistry, 1981, 20,5056–61.

34) Uhlmann E.; Peyman A. Antisense Oligonucleotides: A new Therapeutic Principle. Chemical Reviews, 1990, 90,543.

35) Vlassov, V. V.;Zarytova, V. F.; Kutiavin, I. V.; Mamaev, S. V.; Podyminogin, M. A. Complementary addressed modification cleavage of single strand DNA with alkylating oligonucleotide derivatives. Nucleic Acid Res., 1986, 14, 4065–4076.

36) Volkov, E. M.; Romanowa, E. A.; Krug, A.; Oretskaya, T. S.; Potapov, V. K.; Shabarova, Z. A. Bioorg. Khim., 1988, 14, 1034.

37) Zamecnik, P. C.; Stephenson, M. L. Inhibition of Rous sarcoma virus replication and cell transformation by a specific deoxyoligonucleotide. Proc. Nat. Acad. Sci., USA, 1978, 75, 280–294.

What is claimed is:

1. A compound having the formula:

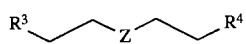

wherein
- $R^3$ is a suitable protecting group;
- Z is —SO$_2$— or —S—S—;
- $R^4$ is —OH, a H-phosphonate, an alkane-phosphonate, a phosphite diester, a phosphite triester, a phosphotriester, a phosphorothioate, a phosphorodithioate, a phosphoroamidate, or a phosphoroamidite.

2. The compound of claim 1, wherein the protecting group is —OR$^1$, wherein $R^1$ is 4,4'-dimethoxyltrityl 3. The compound of claim 1, wherein the phosphoroamidite is —O—P(OCH$_2$CH$_2$CN)—N (C$_3$H)$_2$.

* * * * *

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
( A ) LENGTH: 23 base pairs (B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:1:

AGAAATGGAA AAGGAAGGGA AAA  23

(2) INFORMATION FOR SEQ ID NO:2:

(i) SEQUENCE CHARACTERISTICS:
(A) LENGTH: 17 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:2:

AGAAGAAGAG GTAGTAA  17

(2) INFORMATION FOR SEQ ID NO:3:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:3:

TTCCTCCTGC GG  12

(2) INFORMATION FOR SEQ ID NO:4:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:4:

CCCGGCCTGC GA  12

(2) INFORMATION FOR SEQ ID NO:5:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:5:

AATGGTAAAA TGG  13

(2) INFORMATION FOR SEQ ID NO:6:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid ( x i ) SEQUENCE DESCRIPTION: SEQ ID NO:6:

TTCCTCCTGC GG                                                                                               1 2

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

CCCGGCCTGC GA                                                                                               1 2

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

CGGTGGCGCT GCGCAAGGTA AAACGC                                                                                2 6

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

ACACGAATTT TATTTAATAC                                                                                       2 0

( 2 ) INFORMATION FOR SEQ ID NO:10:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

ATGACTGAAT A                                                                                                1 1

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

GGCGCTGCGC AAGGTAAAA                                                                                        1 9

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

AGGAGAAAGA GA                                    12

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

AGAAGAAGAA GG                                    12

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

AAAAAGAAA AAA                                   13

( 2 ) INFORMATION FOR SEQ ID NO:15:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

AAAAAGGAA AAGG                                 14

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

GGAGGAAAAA GAGA                                14

( 2 ) INFORMATION FOR SEQ ID NO:17:

( i ) SEQUENCE CHARACTERISTICS:
        ( A ) LENGTH: 14 base pairs (B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:17:

GGAGAAAGGA GAGA    14

(2) INFORMATION FOR SEQ ID NO:18:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:18:

AGAGAGAAAA AAGAG    15

(2) INFORMATION FOR SEQ ID NO:19:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:19:

AAGAGGAGGA GGAGG    15

(2) INFORMATION FOR SEQ ID NO:20:

(i) SEQUENCE CHARACTERISTICS:
(A) LENGTH: 16 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:20:

AGGGGGAAAG AAAAAA    16

(2) INFORMATION FOR SEQ ID NO:21:

(i) SEQUENCE CHARACTERISTICS:
(A) LENGTH: 16 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:21:

AAAAGAAAAG GGGGGA    16

(2) INFORMATION FOR SEQ ID NO:22:

(i) SEQUENCE CHARACTERISTICS:
(A) LENGTH: 16 base pairs
(B) TYPE: nucleic acid
(C) STRANDEDNESS: double
(D) TOPOLOGY: linear (ii) MOLECULE TYPE: DNA (genomic)

( x i ) SEQUENCE DESCRIPTION: SEQ ID NO:22:

AAAAGAAAAG GGGGGA     16

( 2 ) INFORMATION FOR SEQ ID NO:23:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:23:

GGAAAAGGAA GGGAAAA     17

( 2 ) INFORMATION FOR SEQ ID NO:24:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

GGCAGAAGAA GAGG     14

( 2 ) INFORMATION FOR SEQ ID NO:25:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

AAGAAAAGAA TGAA     14

( 2 ) INFORMATION FOR SEQ ID NO:26:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

AAGATAGAGG AAGAG     15

( 2 ) INFORMATION FOR SEQ ID NO:27:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

AGAGGAAGAG CAAAA     15

( 2 ) INFORMATION FOR SEQ ID NO:28:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

AGGAAGAAGC GGAGA                                                                   15

( 2 ) INFORMATION FOR SEQ ID NO:29:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

GAAAGCGAAA GGGAAA                                                                16

( 2 ) INFORMATION FOR SEQ ID NO:30:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

AAAAGTAAGA AAAAAG                                                              16

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:31:

GAGAGTGAAG GAGAAA                                                           16

( 2 ) INFORMATION FOR SEQ ID NO:32:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:32:

AGAAGGAGAG AGATGGG                                                       17

( 2 ) INFORMATION FOR SEQ ID NO:33:

( i ) SEQUENCE CHARACTERISTICS:
        ( A ) LENGTH: 17 base pairs (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:33:

AATAAAAAAG GAAAAGG                                                                  17

(2) INFORMATION FOR SEQ ID NO:34:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:34:

AAGAAGAAAA GCAAAGA                                                                  17

(2) INFORMATION FOR SEQ ID NO:35:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:35:

GCAGAGAGAA AAAAGAG                                                                  17

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:36:

GAAGGAATAG AAGAAGAAGG                                                               20

(2) INFORMATION FOR SEQ ID NO:37:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:37:

AAGAGGAGGA GGAGGTGGG                                                                19

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (i i) MOLECULE TYPE: DNA (genomic)

( x i ) SEQUENCE DESCRIPTION: SEQ ID NO:38:

GGAGAAAGGA GAGATAAAAA A  21

( 2 ) INFORMATION FOR SEQ ID NO:39:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:39:

AGAAGAAGAA GGTGGAGAGA GAGA  24

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:40:

AAGAAAAGAA TGAACAAGAA  20

( 2 ) INFORMATION FOR SEQ ID NO:41:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:41:

GAAGGAATAG AAGAAGAAGG TGGAGAGAGA GA  32

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:42:

CGTGCCTTCC CGCAGGAGGA ACGTCCTCGT  30

( 2 ) INFORMATION FOR SEQ ID NO:43:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:43:

CGCGCTTTCT CGCAGGCCGG GCGCCGCCTT  30